(12) United States Patent
Avellanet et al.

(10) Patent No.: US 7,083,632 B2
(45) Date of Patent: Aug. 1, 2006

(54) ANEURYSM EMBOLIC DEVICE WITH AN OCCLUSIVE MEMBER

(75) Inventors: Ernesto Avellanet, Miami Lakes, FL (US); Robert Lulo, Pembroke Pines, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 1574 days.

(21) Appl. No.: 10/295,196

(22) Filed: Nov. 15, 2002

(65) Prior Publication Data

US 2003/0093097 A1 May 15, 2003

Related U.S. Application Data

(60) Provisional application No. 60/335,489, filed on Nov. 15, 2001.

(51) Int. Cl.
*A61B 17/08* (2006.01)

(52) U.S. Cl. .................................. 606/157

(58) Field of Classification Search ........... 606/157, 606/191, 195, 194, 198, 213, 200, 127, 128, 606/110, 113, 114, 151, 282, 96, 104, 105, 606/106, 107, 108
See application file for complete search history.

(56) References Cited

U.S. PATENT DOCUMENTS

| | | | | |
|---|---|---|---|---|
| 5,192,290 A | * | 3/1993 | Hilal | ............. 606/159 |
| 5,192,301 A | | 3/1993 | Kamiya et al. | |
| 5,334,210 A | * | 8/1994 | Gianturco | ............. 606/151 |
| 5,582,619 A | * | 12/1996 | Ken | ............. 606/191 |
| 5,645,566 A | * | 7/1997 | Brenneman et al. | ......... 606/213 |
| 5,733,294 A | | 3/1998 | Forber et al. | |
| 5,823,198 A | | 10/1998 | Jones et al. | |
| 5,904,703 A | * | 5/1999 | Gilson | ............. 606/213 |
| 5,928,260 A | | 7/1999 | Chin et al. | |
| 5,951,599 A | | 9/1999 | McCrory | |
| 6,036,720 A | | 3/2000 | Abrams et al. | |
| 6,063,070 A | | 5/2000 | Eder | |
| 6,063,100 A | * | 5/2000 | Diaz et al. | ............. 606/191 |
| 6,063,111 A | | 5/2000 | Hieshima et al. | |
| 6,113,622 A | | 9/2000 | Hieshima | |
| 6,165,193 A | | 12/2000 | Greene, Jr. et al. | |
| 6,168,622 B1 | | 1/2001 | Mazzocchi | |
| 6,171,329 B1 | | 1/2001 | Shaw et al. | |

(Continued)

FOREIGN PATENT DOCUMENTS

WO    WO 99/05977 A1    11/1999

(Continued)

OTHER PUBLICATIONS

European Search Report dated Oct. 21, 2003, for European Patent Application No. 02257894.2.

*Primary Examiner*—Julian W. Woo
*Assistant Examiner*—Victor Nguyen
(74) *Attorney, Agent, or Firm*—Henry W. Collins

(57) ABSTRACT

An aneurysm embolic device is disclosed for use in occluding the flow of blood within an aneurysm. The aneurysm embolic device includes an expandable sealing member having a circular joining member and reinforcing spokes which give the sealing member a slightly cupped configuration. The embolic device also includes an occlusive member carried by the expandable sealing member. When the aneurysm embolic device is deployed within the aneurysm, the sealing member expands and the occlusive member fills the aneurysm preventing the flow of blood within the aneurysm.

2 Claims, 4 Drawing Sheets

U.S. PATENT DOCUMENTS

| | | |
|---|---|---|
| 6,183,491 B1 | 2/2001 | Lulo |
| 6,193,708 B1 | 2/2001 | Ken et al. |
| 6,214,029 B1 | 4/2001 | Thill et al. |
| 6,254,612 B1 | 7/2001 | Hieshima |
| 6,309,367 B1 | 10/2001 | Boock |
| 6,428,558 B1 | 8/2002 | Jones et al. |

FOREIGN PATENT DOCUMENTS

| | | |
|---|---|---|
| WO | WO 00/13593 A1 | 3/2000 |
| WO | WO 01/30267 A1 | 5/2001 |

\* cited by examiner

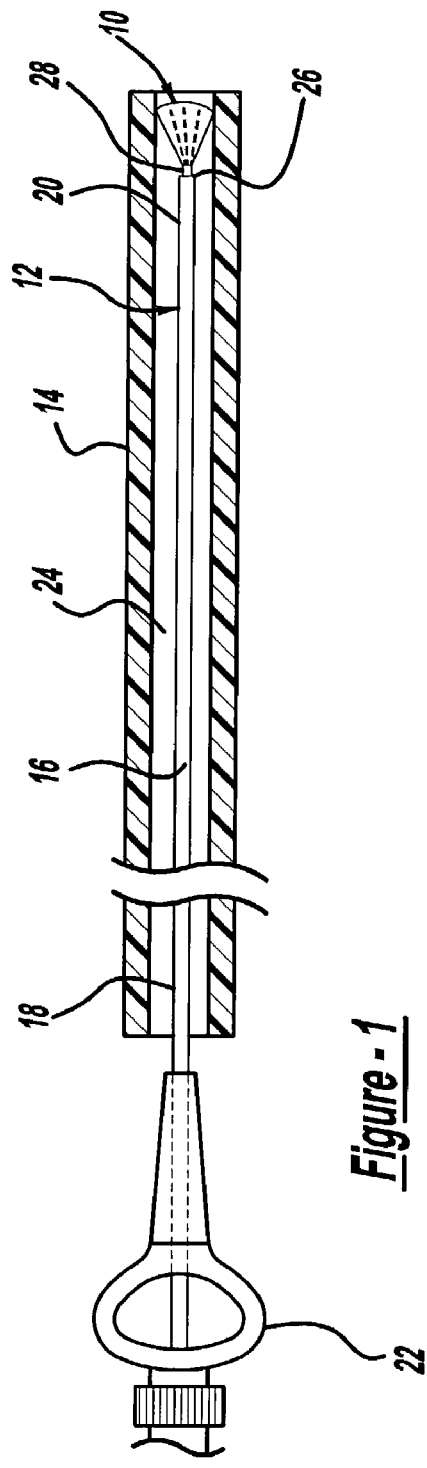
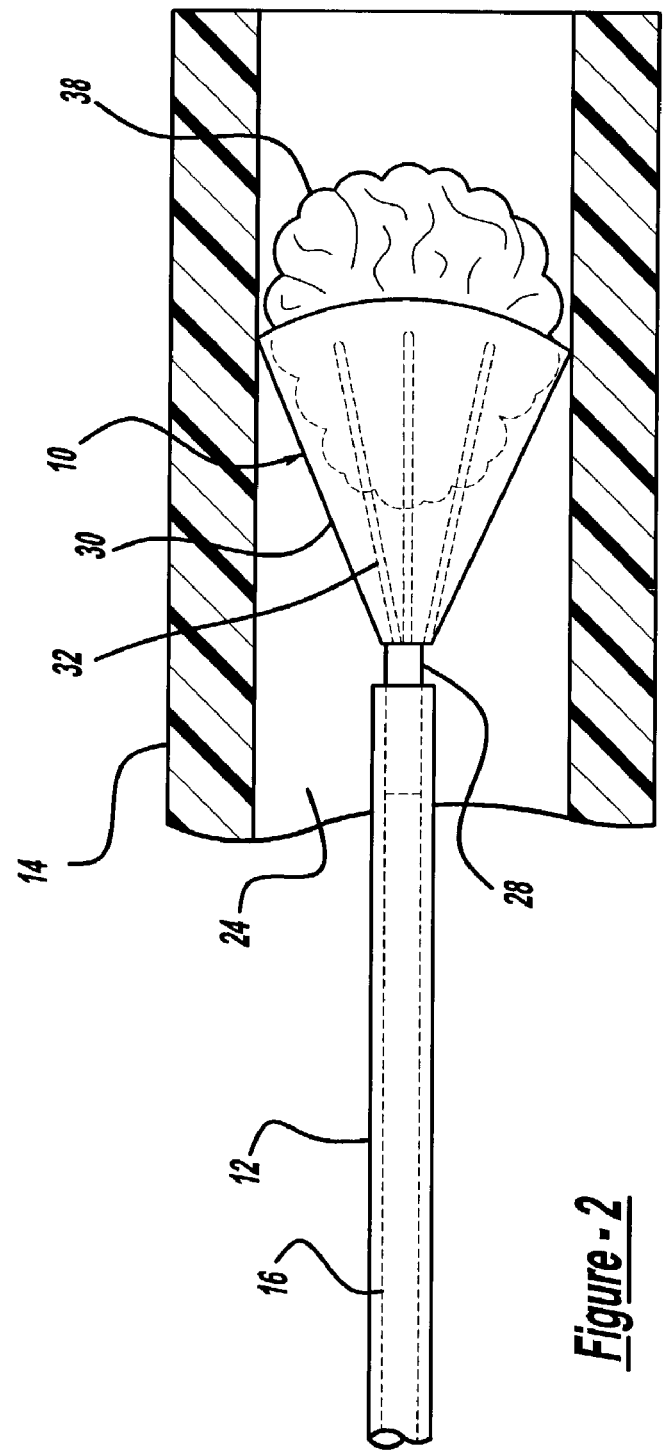
Figure - 1
Figure - 2

ANEURYSM EMBOLIC DEVICE WITH AN OCCLUSIVE MEMBER

This patent application claims the benefit of provisional patent application Ser. No. 60/335,489 filed on Nov. 15, 2001.

BACKGROUND OF THE INVENTION

1. Field of the Invention

This invention relates to catheter-based implantable medical devices for occluding the flow of blood at a preselected position within a blood vessel, and more particularly to an aneurysm embolic device which serves to fill an aneurysm with an occlusive member thereby preventing the flow of blood into the aneurysm.

2. Description of the Prior Art

Aneurysms typically take the form of a balloon-like swelling in the wall of a vessel which generally results from a weakness in the vessel wall. If untreated, aneurysms may continue expanding until they burst thereby causing hemorrhaging to occur. If, for example, an aneurysm is present within an artery of the brain, and the aneurysm should burst with resulting cranial hemorrhaging, death could occur.

Aneurysms result from many different causes; however, most aneurysms are caused as a result of a degenerative disease which damages the muscular coating of a vessel with resulting congenital deficiency in the muscular wall of the vessel.

Various attempts have been made to treat aneurysms without resorting to surgery, such as the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Balloon expandable stents and self-expanding stents are generally delivered to a preselected position through a delivery catheter. They are moved out of the distal end of the delivery catheter, are expanded and then are released to remain within the vessel. One example of a delivery catheter system which may be used to place a stent within a vessel is disclosed in U.S. Pat. No. 6,254,612 entitled, "Hydraulic Stent Deployment System" and assigned to the same assignee as the present patent application. The stent deployment system disclosed in this patent, which is incorporated herein by reference, includes a deployment catheter having a distal tip for retaining a stent in order to transport the stent to a preselected position within the vessel. Once the stent has been properly positioned, a hydraulic control mechanism is used to release the stent from the distal end of the catheter and deposit the stent at the preselected location within the vessel.

Another method for treating aneurysms, particularly where the aneurysm occurs in a very small vessel of the brain, is that of using a microcatheter for placing multiple very small embolic coils within the aneurysm with the expectation that fibrous material will become entrapped in the embolic coils to thereby stabilize the coils within the aneurysm. With this technique, it is possible to fill the aneurysm with embolic coils thereby sealing off the walls of the aneurysm from the pressure of blood which exist in the adjacent vessel.

Examples of a catheter deployment system for depositing embolic coils into an aneurysm are disclosed in U.S. Pat. No. 6,063,100, entitled, "Embolic Coil Deployment System With Improved Embolic Coil"; U.S. Pat. No. 6,183,491 entitled, "Embolic Coil Deployment System With Improved Embolic Coil"; and U.S. Pat. No. 6,113,622 entitled, "Embolic Coil Hydraulic Deployment System," all of which are assigned to the assignee of the present patent application. These patents, and the disclosure thereof, are incorporated herein by reference and made a part of the present patent application.

One modification to the technique of placing embolic coils within an aneurysm is that of using a stent or scaffold like structure which is placed across the aneurysm by having passageways within the structures so that embolic coils may be passed through the structure and into the aneurysm. The stent, or scaffold like structure, serves to hold the embolic coils within the stent until such time as these coils become stabilized by fibrous material growing into the coils. One example of such a structure, or stent, for use in this form of treatment of an aneurysm is disclosed in U.S. Pat. No. 6,063,111 entitled, "Stent Aneurysm Treatment System And Method."

Still another method of treating an aneurysm, and in particular an aneurysm within the brain, is that of placing a mesh covered support structure within the aneurysm itself and subsequently expanding the mesh covered structure in order to fill the entire aneurysm. Such a structure serves to fill the aneurysm and thereby prevent blood flowing in an adjacent vessel from entering the aneurysm. These devices, referred to as occlusion devices, serve to prevent the pressure of blood flowing through a vessel from being applied to the walls of the aneurysm thereby preventing, or reducing, the further expansion of the aneurysm.

One such aneurysm occlusion or embolization device is disclosed in U.S. patent application Ser. No. 09/505,231 entitled, "Aneurysm Embolization Device," and assigned to the same assignee as the present patent application.

Even with the existing treatment techniques for aneurysms, and in particular for aneurysm which exists within the brain, there is a need for other forms of aneurysm treatment that may be easily delivered to a vascular site through a very small catheter, and in particular for a device which serves to seal off the flow of blood between an adjacent vessel and an aneurysm.

SUMMARY OF THE INVENTION

In accordance with one aspect of the present invention, there is provided a catheter-based aneurysm embolic system for occluding the flow of blood into an aneurysm. The aneurysm embolic system includes a deployment catheter. The embolic system also includes an introducer sheath which is disposed about the deployment catheter. The embolic system further includes an aneurysm embolic device which includes an expandable sealing member and an occlusive member which takes the form of an expandable foam material.

The sealing member is preferably an expandable flexible disk and is comprised of a circular joining member located at the center of the sealing member. A plurality of reinforcing spokes are attached to the circular joining member and extend radially outward from the circular joining member. A thin circular membrane is bonded to the circular joining member and the reinforcing spokes, and an occlusive member, such as an expandable foam, is carried by the sealing member. In addition, a headpiece is attached to the center of the sealing member and is disposed in the distal end of the deployment catheter. When the aneurysm embolic device is placed at the neck of an aneurysm the sealing member may be expanded to seal the mouth of the aneurysm and simultaneously permit deployment of the occlusive member within the aneurysm to substantially fill the aneurysm.

In accordance with another aspect of the present invention, the occlusive member is formed of a material such that when the sealing member is deployed within an aneurysm the occlusive member may be released within the aneurysm and the material expands to substantially fill the aneurysm.

In accordance with a further aspect of the present invention, the aneurysm embolic device includes first and second circular membranes having surfaces which are bonded together and which encapsulate the circular joining member and the reinforcing spokes. The circular membrane is preferably made from a blood-impermeable polymer material.

In accordance with still another aspect of the present invention, the expandable sealing member is slightly cupped to form convex and concave sides. The occlusive member is attached to the concave side of the sealing member.

In accordance with another aspect of the present invention, the expandable sealing member is tubular shaped when the sealing member is disposed within the lumen of the sheath.

BRIEF DESCRIPTION OF THE DRAWINGS

FIG. 1 is an enlarged perspective view of an aneurysm embolic device, a deployment catheter, and a sheath in accordance with the present invention;

FIG. 2 is an enlarged, sectional view of the aneurysm embolic device in a compressed configuration within a lumen of the sheath and attached to a distal end of the deployment catheter;

DESCRIPTION OF THE PREFERRED EMBODIMENT

Figure 3A:
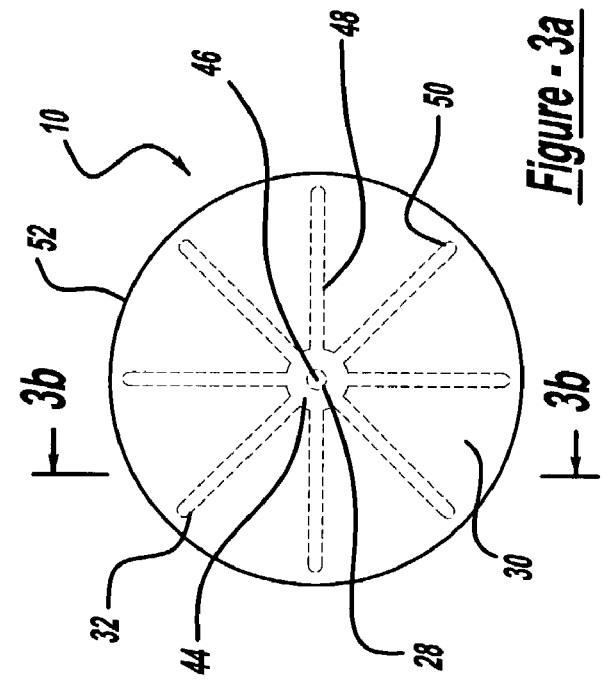
FIG. 3a is an enlarged, perspective view of the aneurysm embolic device as viewed from a distal end of the deployment catheter.

FIG. 1 illustrates an aneurysm embolic device 10, a deployment catheter 12, and a sheath 14 in accordance with the present invention. The deployment catheter 12 is an elongated tube with a lumen 16. Preferably, the proximal section 18 of the deployment catheter 12 is formed of a pellethane material having a durometer in a range of about 60D to 75D. The proximal section 18 is sufficiently flexible to transverse the vasculature of the human body, but is sufficiently rigid so that it can be pushed distally through the sheath 14. The distal section 20 of the deployment catheter 12 is preferably formed of a pellethane material having a durometer of between 25D and 55D with a durometer of 40D being the preferred durometer.

The deployment catheter 12 also includes a winged hub 22 coupled to the proximal section 18 of the deployment catheter 12. The winged hub 22 may be made from plastic and aids in the insertion of the deployment catheter 12 into the vasculature of the body. The sheath 14 is also an elongated tube with a lumen 24 extending therethrough. The sheath 14 is preferably formed of a polymer material and is sufficiently flexible to transverse the vasculature of the body. The deployment catheter 12 and aneurysm embolic device 10 are disposed within the lumen 24 of the sheath 14. The diameter of the lumen 24 on the sheath 14 is sufficiently small enough so that the aneurysm embolic device 10 is forced to a compressed configuration. The aneurysm embolic device 10 is attached to the distal end 26 of the deployment catheter 12 by way of a headpiece 28 which is described in more detail below.

FIG. 2 illustrates the aneurysm embolic device 10 in a compressed configuration within the lumen 24 of the sheath 14. The aneurysm embolic device 10 includes an expandable sealing member 30. When compressed, the expandable sealing member 30 is generally tube-shaped such that the aneurysm embolic device 10 may be disposed within a sheath 14. The aneurysm embolic device 10 also includes a plurality of longitudinal reinforcing spokes 32 within the expandable sealing member 30. These reinforcing spokes 32 are discussed in the description of FIG. 3a. The headpiece 28 is attached to the sealing member 30 and is disposed within the distal end 26 of the deployment catheter 12. The headpiece 28 forms a fluid tight seal in the distal end 26 of the deployment catheter 12 so that when a fluid pressure is applied to the lumen 16 of the deployment catheter 12, the headpiece 28 is released from the distal end 26 of the deployment catheter 12.

Figure 3:
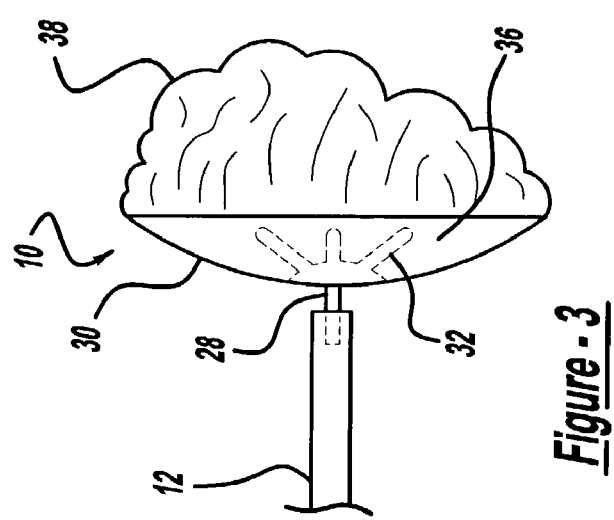
FIG. 3 is an enlarged, perspective view of the aneurysm embolic device in a deployed configuration showing an expanded occlusive member.

FIG. 3 illustrates the aneurysm embolic device 10 in a deployed configuration. The expandable sealing member 30 is preferably made of a flexible material like a polymer, silicon, or fabric, but may also be formed from a metallic material such as platinum or Nitinol. The expandable sealing member 30 may also include radiopaque material for fluoroscopic visualization. Preferably, the sealing member 30 is slightly cupped so that when the sealing member 30 is deployed within an aneurysm, the convex side 36 of the sealing member 30 conforms to a wall of the aneurysm. The diameter of the sealing member 30 is preferably slightly larger than the diameter of an opening of the aneurysm 34. Typically, the sealing member 30 will seal the opening of a 5 to 6 mm aneurysm, but may be increased in size to seal aneurysms in the range of 3 to 20 mm.

Figure 5:
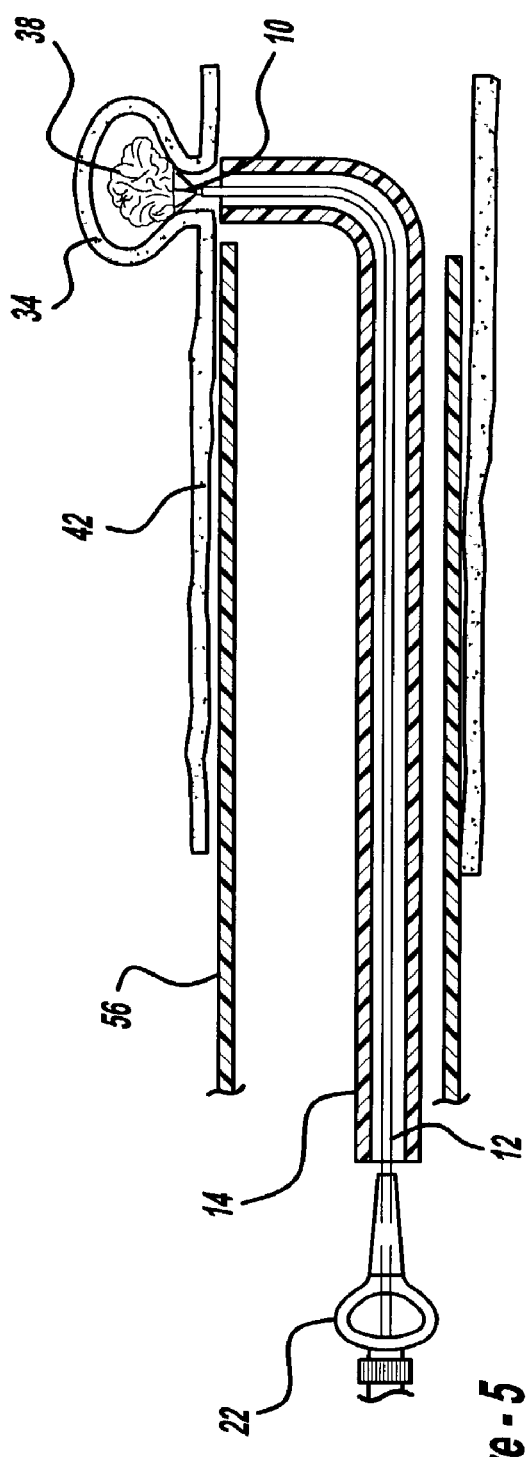
FIG. 5 is an enlarged, sectional view of the aneurysm embolic device being deployed within the aneurysm; and, FIG. 6 is an enlarged, sectional view of the aneurysm embolic device in its deployed configuration with the occlusive member substantially filling the aneurysm.

The occlusive member 38 is compressed when the aneurysm embolic device 10 is disposed within the lumen 24 of the sheath 14. When the aneurysm embolic device 10 is deployed, the occlusive member 38 is released into an aneurysm 34 as illustrated in FIG. 5. The sealing member 30 occludes the mouth of the aneurysm 34 and prevents the occlusive member 38 from exiting the aneurysm 34. The occlusive member 38 is preferably polyvinyl alcohol, but may also be nylon fibers, biocompatible foam, biocompatible adhesive, embolic coils, or an expandable material, such as for example, hydrogel. As the occlusive member 38 is deployed within the aneurysm 34, the convex side 36 of the sealing member 30 forms a generally fluid tight seal around the interior opening of the aneurysm 34. The occlusive member 38 may be anchored to the aneurysm embolic device 10 or preferably may rest freely within the compressed aneurysm embolic device 10 until deployed.

FIG. 3a illustrates the aneurysm embolic device 10 in a deployed configuration as viewed from within a blood vessel adjacent to the aneurysm 34. A thin circular joining member 44 is disposed at the center 46 of the sealing member 30. The circular joining member 44 may be made of stainless steel, titanium, platinum, or a polymer material, but the preferred material is Nitinol. A plurality of reinforcing spokes 32 extends radially outward from the circular joining member 44. The proximal ends 48 of each reinforcing spoke are attached to the circular joining member 44, while the distal ends 50 of each reinforcing spoke 32 extend generally to the outer edge 52 of the sealing member 30.

Preferably, the reinforcing spokes 32 may be made of the same material as the circular joining member 44. The reinforcing spokes 32 may take the form of cylindrical rods, flat battens, or rectangular rods. Preferably, the circular joining member 44 and the reinforcing spokes 32 are one unitary structure laser cut from Nitinol. The headpiece 28 may also be cut from the same unitary Nitinol structure. The circular joining member 44 and the reinforcing spokes 32 may include radiopaque markers for use during fluoroscopic visualization.

Figure 3B:
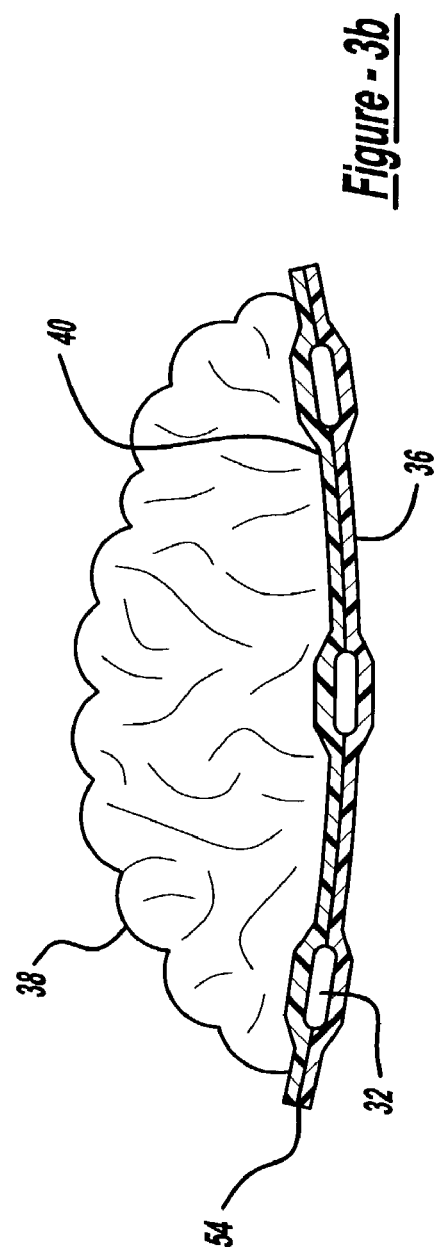
FIG. 3b is an enlarged, cross sectional view of the aneurysm embolic device showing reinforcing spokes encapsulated between two thin circular membranes and the expanded occlusive member disposed on the circular membranes.

FIG. 3b illustrates the slightly cupped configuration of the expandable sealing member 30. The curvature may be created by a normally curved sealing member 30, but preferably, the curvature is formed by normally curved reinforcing spokes 32. Two thin circular membranes 54 are bonded to the reinforcing spokes 32 and the circular joining member 44 (not shown). Preferably, one circular membrane 54 may be attached to the reinforcing spokes 32 on the concave side 40 of the sealing member 30 while the other circular membrane 54 may be attached to the reinforcing spokes 32 on the convex side 36 of the sealing member 30, such that the circular membranes 54 encapsulate the reinforcing spokes 32 and the circular joining member 44. The occlusive member 38 is disposed on the concave side 40 of the expandable sealing member 30.

Figure 4:
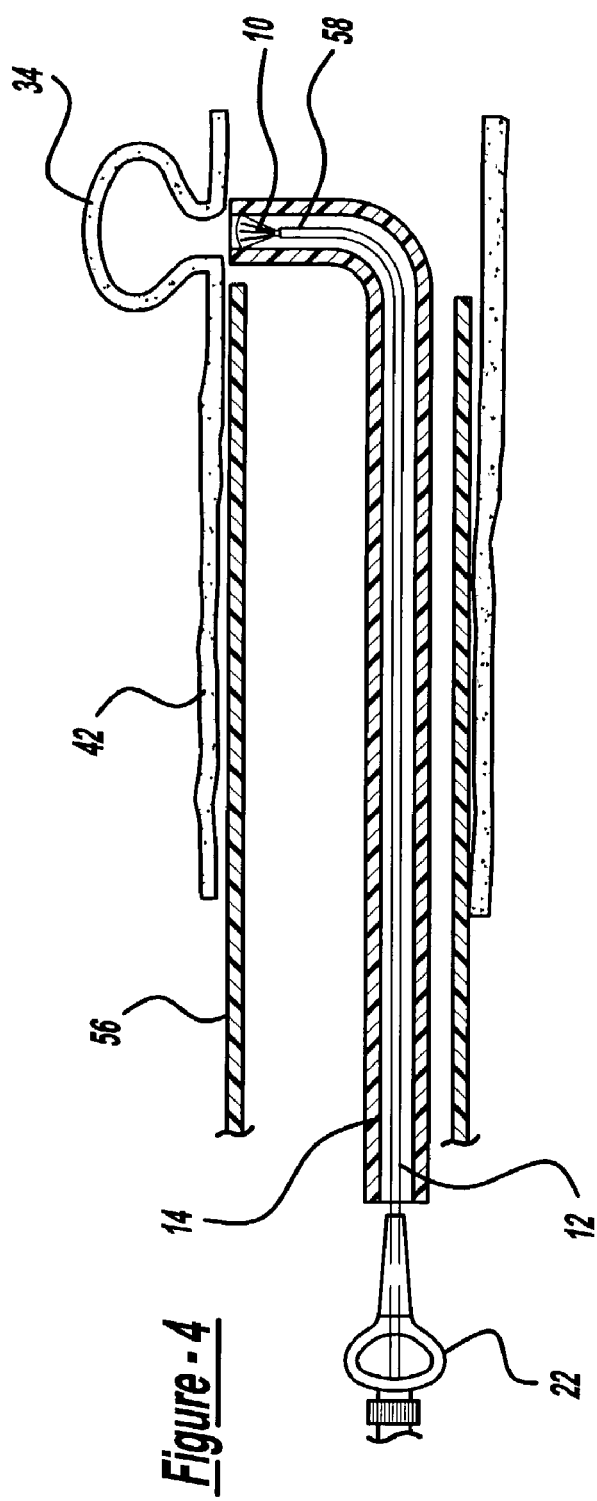
FIG. 4 is an enlarged, sectional view of the aneurysm embolic device in its compressed configuration being positioned over an aneurysm.
Figure 6:
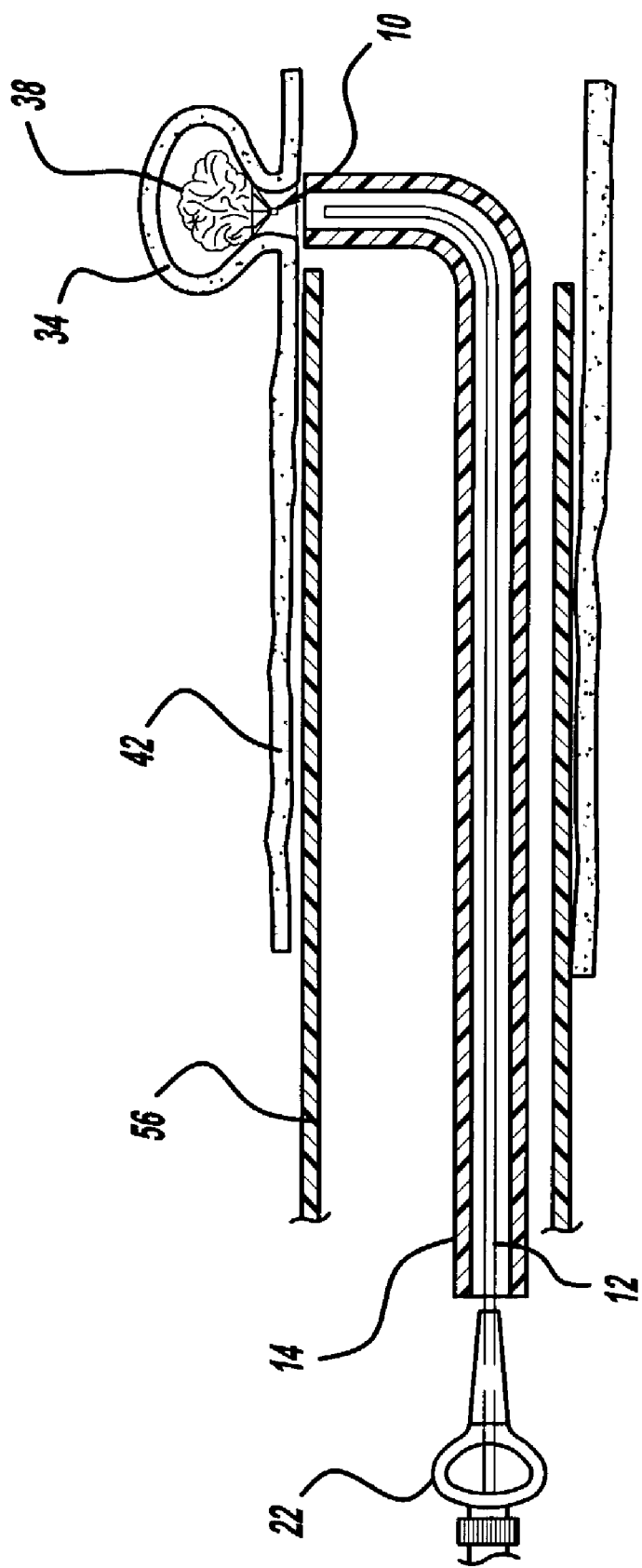

FIGS. 4 through 6 illustrate the deployment of the aneurysm embolic device 10 within the aneurysm 34. FIG. 4 illustrates the aneurysm embolic device 10, the deployment catheter 12, and sheath 14 being positioned within the blood vessel 42 adjacent to the aneurysm 34 to be treated. The headpiece 28 of the aneurysm embolic device 10 is disposed within the lumen 16 of the deployment catheter 12, and the aneurysm embolic device 10 is disposed within the sheath 14 so that the sealing member 30 is in a compressed configuration. This allows the aneurysm embolic device 10 to hold the occlusive member 38 and to be transported through the narrow vasculature. A delivery catheter 56 is positioned within the vasculature to guide the deployment catheter 12 to the preselected aneurysm 34 and to protect the vasculature from damage or puncture.

FIG. 5 illustrates the distal end 58 of the sheath 14 being positioned at the mouth of the aneurysm 34. The deployment catheter 12 is moved distally causing the sealing member 30 of the aneurysm embolic device 10 to exit the lumen 24 of the sheath 14. Without the sheath 14 maintaining the aneurysm embolic device 10 in a compressed configuration, the sealing member 30 and occlusive member 38 expand within the aneurysm 34. The thin circular membranes 54 of the sealing member 30 contact the wall of the aneurysm 34 and form a generally fluid tight seal.

FIG. 6 illustrates fluid pressure being applied to the lumen 16 of the deployment catheter 12 thereby causing the headpiece 28 of the aneurysm embolic device 10 to exit the distal end 26 of the deployment catheter 12. The expanded occlusive member 38 holds the sealing member 30 in position, and blood is generally prevented from flowing into the aneurysm 34.

A novel system has been disclosed in which an aneurysm embolic device is used to occlude the flow of blood within an aneurysm. Although a preferred embodiment of the invention has been described, it is to be understood that various modifications may be made by those skilled in the art without departing from the scope of the present invention. For example, there are many variations and modifications of the occlusive member, including helically wound embolic coils or other types of vascular occlusive devices, such as balloons, radiopaque fluids, and liquid medications.

These and other modifications would be apparent to those having ordinary skill in the art to which this invention relates and are intended to be within the scope of the claims which follow.

That which is claimed is:

1. A catheter-based aneurysm embolic system for occluding the flow of blood in an aneurysm, said aneurysm embolic system comprising:
   a deployment catheter having a lumen extending therethrough and having proximal and distal ends;
   an aneurysm embolic device comprising an expandable sealing member which includes a circular joining member, a plurality of reinforcing spokes attached to said circular joining member and extending radially outward from said circular joining member, and a thin circular membrane bonded to said circular joining member and said reinforcing spokes and an occlusive member comprised of an expandable foam material carried by said sealing member, and a headpiece attached to the sealing member and retained by the distal end of said deployment catheter so that when said aneurysm embolic device is placed at the neck of an aneurysm said sealing member may be expanded to seal the mouth of the aneurysm and simultaneously permit expansion of said occlusive member within the aneurysm to thereby substantially fill the aneurysm, said embolic device also includes a first and second circular membrane having surfaces which are bonded together and which encapsulate said circular joining member and said reinforcing spokes.

2. An aneurysm embolic device for occluding the flow of blood in an aneurysm, said aneurysm embolic device comprising:
   an expandable sealing member including a circular joining member, a plurality of reinforcing spokes being attached to said circular joining member and extending radially outward from said circular joining member, a thin circular membrane bonded to said circular joining member and said reinforcing spokes, said embolic device also includes a first and second circular membrane having surfaces which are bonded together and which encapsulate said circular joining member and said reinforcing spokes; and,
   an expandable foam occlusive member carried by said sealing member so that upon expansion of said expandable sealing member said expandable foam simultaneously expands to fill an aneurysm.

* * * * *